United States Patent [19]

Guth et al.

[11] Patent Number: 5,399,336

[45] Date of Patent: * Mar. 21, 1995

[54] STANNOZEOSILITE/ZIRCONOZEOSILITE ZEOLITES AND CATALYTIC HYDROXYLATION OF PHENOLICS THEREWITH

[75] Inventors: Jean-Louis Guth, Brunstatt; Michel Costantini, Lyons; Annie Lopez, Saint Wandrille Rancon; Jean-Michel Popa, Drancy, all of France

[73] Assignee: Rhone-Poulenc Chimie, Courbevoie, France

[*] Notice: The portion of the term of this patent subsequent to Sep. 21, 2010 has been disclaimed.

[21] Appl. No.: 724,215

[22] Filed: Jul. 1, 1991

[30] Foreign Application Priority Data

Jun. 29, 1990 [FR] France ................... 90 08210
Jun. 29, 1990 [FR] France ................... 90 08209
Aug. 31, 1990 [FR] France ................... 90 10872

[51] Int. Cl.$^6$ ..................... C01B 33/20; B01J 29/04
[52] U.S. Cl. ..................... 423/705; 423/326; 423/704; 502/64
[58] Field of Search ............ 423/326, 705, 704; 502/64

[56] References Cited

U.S. PATENT DOCUMENTS

| | | | |
|---|---|---|---|
| 3,941,871 | 3/1976 | Dwyer et al. | 423/705 |
| 4,564,511 | 1/1986 | Desmond et al. | 423/713 |
| 4,941,963 | 7/1990 | Valyocsik | 423/706 |
| 5,082,641 | 1/1992 | Popa et al. | 423/705 |
| 5,110,571 | 5/1992 | Corcoran, Jr. et al. | 423/326 |
| 5,246,688 | 9/1993 | Faust et al. | 423/704 |

FOREIGN PATENT DOCUMENTS

| | | |
|---|---|---|
| 1192891 | 9/1985 | Canada ................... 423/328 |
| 1196903 | 11/1985 | Canada ................... 423/328 |
| 77523 | 4/1983 | European Pat. Off. . |
| 94288 | 11/1983 | European Pat. Off. . |
| 292363 | 11/1988 | European Pat. Off. . |
| 0306214 | 3/1989 | European Pat. Off. . |
| 0321177 | 6/1989 | European Pat. Off. . |
| 337835 | 10/1989 | European Pat. Off. . |
| 0346250 | 12/1989 | European Pat. Off. . |
| 2116974 | 10/1983 | United Kingdom . |

OTHER PUBLICATIONS

Chemical Abstracts, vol. 112, No. 26, 25 Jun. 1990, p. 136, resume No. 237640c, Columbus, Ohio, US, W. Pang et al "Preparation of tin–ZSM–5 type zeolite by gas–solid substitution reaction", & Shiyou Xuebao, Shiyou Jiagong 1989, 5(2), 93–8.

*Primary Examiner*—Anthony McFarlane
*Attorney, Agent, or Firm*—Burns, Doane, Swecker & Mathis

[57] ABSTRACT

Calcined silica/oxide zeolites, characteristically MFI stannozeosilites or zirconozeosilites, well adopted for catalyzing the $H_2O_2$ hydroxylation of phenols or phenol ethers, have the formula (I):

$$(Si_{96-x}T'_x)O_{192} \qquad (I)$$

in which x is a number ranging from 0.1 to 5.0 and T' is tetravalent tin or tetravalent zirconium.

45 Claims, No Drawings

STANNOZEOSILITE/ZIRCONOZEOSILITE ZEOLITES AND CATALYTIC HYDROXYLATION OF PHENOLICS THEREWITH

BACKGROUND OF THE INVENTION

1. Field of the Invention

The present invention relates to novel zeolites based on silica and oxides of the tetravalent elements tin and zirconium, and, more especially, relates to novel zeolites based on silica and tin oxides and zeolites based on silica and zirconium oxide.

This invention also relates to novel MFI zeolites, to a process for the production thereof, and to the use of such novel MFI zeolites as catalysts in the hydroxylation of phenols or phenol ethers with hydrogen peroxide.

2. Description of the Prior Art

Zeolites are crystallized tectosilicates. Their structures are assemblies of tetrahedra $TO_4$ which constitute a three-dimensional network by sharing oxygen atoms. In zeolites of the aluminosilicate type, which are the most typical, T represents tetravalent silicon and trivalent aluminum. The cavities and channels of molecular dimensions in this network receive cations which compensate for the charge deficit resulting from the presence of trivalent aluminum in the tetrahedra. Trivalent elements such as gallium and more rarely boron or beryllium may be substituted for the aluminum.

In general, the composition of the zeolites may be represented by the empirical formula $M_{2/n}O$; $Y_2O_3$; $xZO_2$ in the dehydrated, calcined state. Z and Y respectively represent the tetravalent and trivalent elements of the tetrahedra $TO_4$; M represents an electropositive element of valency n such as an alkali metal or alkaline earth metal, defining the compensating cations; x may range from 2, theoretically to infinity, in which case the zeolite is a silica.

Each type of zeolite has a distinctive porous structure. The variation in the dimensions and shapes of the pores from one type to another result in changes in the adsorbing properties thereof. Only molecules of certain dimensions and shapes can inlet the pores of a particular zeolite. These unique characteristics of the zeolites make them particularly suitable for purifying or separating mixtures of gases or liquids, for example for separating hydrocarbons by selective adsorption.

Chemical composition, particularly as regards the nature of the elements present in the tetrahedra $TO_4$ and the nature of the exchangeable compensating cations, is also an important factor involved in the selectivity of adsorption and particularly in the catalytic properties of these materials. They are used as catalysts or catalyst carriers in cracking, reforming and modification of hydrocarbons and in the synthesis of a wide variety of chemical species.

Many zeolites are of natural origin; they are aluminosilicates, the availability and properties of which do not always meet the requirements of industrial applications. Continuing research for materials having new proprieties has, consequently, promoted the synthesis of a wide variety of zeolites, essentially of the aluminosilicate type. Exemplary thereof are zeolite A (U.S. Pat. No. 2,882,243), zeolite X (U.S. Pat. No. 2,882,244), zeolite Y (U.S. Pat. No. 3,130,007), zeolite L (FR-A 1,224,154), zeolite T (FR-A 1,223,775), zeolite ZSM5 (U.S. Pat. No. 3,702,886), zeolite ZSM12 (U.S. Pat. No. 3,832,449) and zeolite ZSM48 (EP-A 0,015,132).

The zeolites are typically produced from a reaction mixture which is converted, in a hydrothermal medium, by a process of dissolution/recrystallization. After being separated and dried, the crystalline precipitate is calcined to provide an active zeolite.

The reaction mixture contains reagents which may provide the elements T to be incorporated in the network of the zeolite. These reagents are typically aqueous gels containing oxides or hydroxides of the elements T.

It also contains one or more mobilizing agents to promote dissolution of the reagents and transfer from the aqueous phase to the zeolite crystals which are forming, and a structuring agent which is incorporated to form microporous spaces and to stabilize the zeolite.

$OH^-$ anions are typical mobilizing agents. Thus, the reaction media are then characterized by a basic pH, generally above 10. These media are very appropriate for dissolving sources containing the elements silicon and aluminum and, in general, any elements providing oxygen-containing anions which are soluble in a basic medium.

When strong bases such as alkali metal hydroxides are used, highly supersaturated media are produced, permitting rapid crystallization of the zeolites. But it is often difficult to control the formation of the desired crystallized phase, which is metastable in many instances. On the other hand, a high rate of crystallization may result in the formation of faults within the network of the $TO_4$ tetrahedra, such as -T-O- instead of -T-O-T- bridges. Finally, the presence of alkaline compensating cations in the channels and cavities is often disadvantageous for certain applications, and it may then be necessary to conduct an exchange with other cations. This latter disadvantage may be avoided by replacing the bases by other strong bases, such as alkyl ammonium hydroxides, which may provide a structuring function at the same time. But the high cost of these compounds limits their industrial use. The use of weaker bases such as amines, which also have structuring properties, avoids many of the disadvantages indicated above. In this event, however, the concentration of mobilizing $OH^-$ anions may become too weak, rendering the reaction speeds too low.

Moreover, it is not always easy to incorporate certain metallic species in the $TO_4$ tetrahedra of the network of the zeolite when the reaction medium is basic.

SUMMARY OF THE INVENTION

Accordingly, a major object of the present invention is the provision of novel zeolites based on silica and an oxide of a tetravalent element, in particular a zeolite based on silica and tin oxide and a zeolite based on silica and zirconium oxide, which novel zeolites avoid or conspicuously ameliorate those disadvantages and drawbacks to date characterizing the state of this art.

Another object of this invention is a process for the production of such zeolites from neutral or acid reaction mixtures which enable tin and/or zirconium to be incorporated within the network of the zeolite, and which produces zeolite crystals of completely controlled dimensions.

Briefly, the present invention features zeolites based on silica and the oxides of tetravalent elements, having the following general formula (I), after calcination:

$$(Si_{96-x}T'_x)O_{192} \quad (I)$$

in which x is a number ranging 0.1 to 5.0 and T' is a tetravalent element selected from between tin and zirconium.

DETAILED DESCRIPTION OF THE PREFERRED EMBODIMENTS OF THE INVENTION

More particularly according to the present invention, the subject zeolites are of the pentasil family and are similar to zeolites of the MFI structural type.

The zeolites according to the invention also contain fluorine. The concentration of fluorine typically ranges from 0.01% to 1.3% by weight, prior to calcination.

The zeolites based on silica and tin oxide, designated the stannoseoislites, preferably have the following formula (Ia):

$$(Si_{96-x}Sn_x)O_{192} \quad (Ia)$$

in which x is a number ranging from 0.1 to about 3.0 and preferably from 0.1 to 2.0.

The zeolites based on silica and zirconium oxide, designated the zirconozeosilites, preferably have the formula (Ib):

$$(Si_{96-x}Zr_x)O_{192} \quad (Ib)$$

in which x is a number ranging from 0.1 to about 4.0 and preferably from 0.1 to 2.0.

The present invention also features a process for the synthesis of the above zeolites, comprising:
(i) preparing a reaction mixture in aqueous media containing a silicon source having an oxidation state of +4, a source of tetravalent element T', fluoride ions and a structuring agent; the pH of the reaction mixture ranging from about 1.5 to about 12.0,
(ii) crystallizing the reaction mixture by heating and recovering the crystallized precipitate therefrom, and
(iii) calcining said recovered precipitate at a temperature above 450° C. to remove the structuring agent occluded in the channels thereof.

The pH of the reaction mixture advantageously ranges from 6.0 to 11.0.

The use of fluoride ions in the reaction medium, serving as a mobilizing agent, permits the T species (Si and Sn or Zr) to be solubilized in a medium of synthesis having a pH below 10. Thus, $NH_4^+$ ions can be used as compensating cations; these can, if desired, be completely eliminated during calcination. On the other hand, it is advisable to avoid the presence of alkaline cations in the reaction medium.

Moreover, since crystallization occurs in a reaction medium having a pH below 11, the nucleation speed is lower. Thus, it is possible to produce zeolite crystals having a controlled size by controlling the nucleation speed.

Many sources of the element silicon in an oxidation state of +4 may be used. Exemplary thereof are silicas in the form of hydrogels, aerogels, xerogels, colloidal suspension, silicas obtained by precipitation from solutions of soluble silicates or by hydrolysis of silicic esters, such as $Si(OCH_3)_4$, $Si(OC_2H_5)_4$, silicas prepared by extraction or activation of natural or synthetic, crystallized or amorphous compounds such as aluminum silicates, aluminosilicates or clays. Hydrolyzable compounds of tetravalent silicon may also be used, such as silicon halides, or the like.

Exemplary of the tetravalent elements T' are tin oxide and zirconium oxide, as indicated above.

Exemplary sources of tin oxide are crystallized or amorphous tin oxides and hydroxides, compounds of tetravalent tin which can be hydrolyzed, such as halides ($SnCl_4$), alcoholates and soluble tin salts such as tin nitrate $Sn(NO_3)_4$.

The sources of silica or tin oxide may equally as well be compounds including the elements Si and Sn, such as glasses or gels based on the oxides of these two elements.

Exemplary sources of zirconium oxide are crystallized or amorphous zirconium oxides and hydroxides, compounds of tetravalent zirconium which can be hydrolyzed, such as halides ($ZrCl_4$), alcoholates, soluble salts of zirconium such as zirconium nitrate $(ZrNO_3)_4$ or zirconium sulfate, $Sr(SO_4)_2 \cdot xH_2O$.

Compounds containing the elements Si and Zr, such as the glasses or gels based on the oxides of these two elements, may also be used as sources of silica or zirconium oxide.

The sources of silica and tin oxide and/or zirconium oxide may be used in soluble form, or in the form of powdered solids, and also in the form of conglomerates, such as pellets or extrusions which can be converted into a zeolite of the desired structure without having a change in the shape thereof.

The mobilizing agent $F^-$ is introduced in the form of acid and/or salt(s), devoid of any alkaline cations, and/or of compounds which liberate $F^-$ upon hydrolysis. Exemplary thereof are hydrofluoric acid; hydrofluorides of amines; quaternary ammonium fluorides such as $NH(C_3H_3)_4F$, $N(C_3H_7)_4F$; $SiF_4$; $SnF_4$; $(NH_4)_2SiF_6$.

Ammonium fluoride or acid ammonium fluoride are the preferred salts. They are indeed very soluble and do not introduce any undesirable element. In addition, they can easily be removed after crystallization.

Exemplary structuring agents for carrying out the process of the invention include
(a) tertiary amines of the formula (II):

(II)

wherein $R_1$, $R_2$, and $R_3$, which may be identical or different, are each a straight or branched chain alkyl radical having 1 to 6 carbon atoms, preferably a propyl or butyl radical;
(b) quaternary ammonium salts of the formula (III):

(III)

wherein $R_1$, $R_2$, $R_3$ and $R_4$, which may be identical or different, are each straight or branched chain alkyl radical having 1 to 6 carbon atoms, preferably propyl or butyl radicals; and
(c) compounds of formula (II) or formula (III) in which the nitrogen atom has been replaced by a phosphorus atom.

In a preferred embodiment of the invention, the structuring agents are compounds providing tetrapropyl ammonium or tripropyl ammonium cations.

The structuring agent is advantageously included in the reaction mixture in the form of a quaternary ammonium salt of formula (III), or the amine of formula (II), the pH thereof optionally being adjusted with a base. The base should preferably have weak structuring agent properties, such that it does not compete with the structuring agent added. Exemplary bases which are thus suitable are methylamine, dimethylamine, trimethylamine, ethylamine, diethylamine and triethylamine.

The reaction mixture advantageously has the following composition, expressed as a molar ratio:

T'/(Si+T') ranging from 0.001 to 0.20, preferably from 0.005 to 0.1;

Structuring agent/(Si+T') ranging from 0.002 to 4, preferably from 0.04 to 1;

F/(Si+T') ranging from 0.02 to 6, preferably from 0.06 to 2;

$H_2O$/(Si+T') ranging from 4 to 400, preferably from 10 to 200.

When a base is employed to adjust the pH of the reaction medium, the molar ratio of base to (T'+Si) is preferably less than 12 and more preferably ranges from 0.1 to 8.

The addition of crystallized seeds of specific MFI structure to the reaction mixture, in a proportion not exceeding a few percent by weight relative to the weight of the $SiO_2+T'O_2$, facilitates crystallization of the prior to calcination, hereinafter referred to as "zeolite precursors." They are crystalline products of the zeolite type, based on silica and the oxides of tetravalent elements and having the following formula (IV):

$(Si_{96-x}T'_x)O_{192'},4\pm1(S^+F^-)$  (IV)

in which x is a number ranging from 0.1 to 5.0, $S^+$ is the cation from the structuring agent, and T' is a tetravalent element selected from between tin and zirconium.

The zeolite precursors based on silica and tin oxide preferably have the following formula (IVa):

$(Si_{96-x}Sn_x)O_{192'},4\pm1(S^+F^-)$  (IVa)

in which x is a number ranging from 0.1 to about 3.0 and preferably from 0.1 to 2.0, and $S^+$ is the cation emanating from the structuring agent.

The zeolite precursors based on silica and zirconium oxide preferably have the following formula (IVb):

$(Si_{96-x}Zr_x)O_{192'},4\pm1(S^+F^-)$  (IVb)

in which x is a number ranging from 0.1 to 4.0 and preferably from 0.1 to 2.0, and $S^+$ is the cation emanating from the structuring agent.

$S^+$ more particularly is a cation emanating from the amine of formula (II), a cation of the quaternary ammonium type in the formula (III), or those same compounds wherein the nitrogen atom is replaced by a phosphorus atom.

The MFI zeolite may be identified by determining the X-ray diffraction pattern of the precursor thereof.

The zeolite precursors of the invention have an orthorhombic crystalline system and an X-ray diffraction pattern as indicated in the following Table, for the zeolite precursor based on silica and tin oxide and for that based on zirconium oxide.

The Table reports the extreme values of the various reticular equidistances $d_{hkl}$. They correspond to the concentration limits of the tetravalent element zeolite. The seed crystals may be any zeolite of MFI structure, whatever its chemical composition.

It is preferable to use a zeosilite, which is a zeosilite equivalent to stannozeosilite or zirconozeosilite, but containing only silicon in the network thereof. Seed crystals of stannozeosilite or zirconozeosilite from a prior production run may be used equally as well.

Crystallization of the zeolite may be attained by heating the reaction mixture to a temperature of from about 40° C. to about 240° C., preferably from 60° C. to 220° C., for the period of time required for crystallization, according to conventional technique for synthesizing zeolites, per se known to this art. For example, the heating time may range from 6 hours to about 500 hours.

The heating and crystallization are preferably carried out in an enclosure or autoclave coated with a material such as polytetrafluoroethylene.

The reaction mixture either may or may not be agitated.

After crystallization, the precipitate obtained is recovered, e.g., by filtration.

After an optional drying step, the precipitate is heated to a temperature above 450° C., preferable above 500° C., to decompose the organic species contained in the precipitate, such as the structuring agent, by calcination or thermal decomposition.

A stannozeosilite or, respectively, a zirconozeosilite according to the invention, of MFI structure, is thus produced, depending on whether or not the tetravalent element is tin or zirconium.

As indicated above, the zeolites contain from 0.01% to 1.3% by weight of fluorine. The fluorine may, however, be removed by hydrothermal treatment at a pH above 7, without thereby modifying the structure of the zeolite according to the invention.

The invention also features the zeolites produced incorporated within the network of the zeolite before calcination, or more specifically to the ration T'/(Si+T').

The diffraction pattern can be determined using a diffractometer, using the conventional method of powders with $K\alpha$ radiation of copper. The reticular equidistances $d_{hkl}$ characteristic of the sample are calculated from the position of the diffraction peaks represented by the angle 2θ, by the Bragg equation. The measuring error A ($d_{dkl}$) out of $d_{dkl}$ is estimated by the Bragg equation, as a function of the absolute error Δ(2θ) assigned to the measurement of 2θ. An absolute error Δ(2θ) of ±0.2° is currently permitted. The relative intensity $I/I_o$ assigned to each $d_{hkl}$ value is estimated from the height of the corresponding diffraction peak. A scale of symbols is typically used to characterize this intensity: FF=very high, F=high, mF=medium to high, m=medium, mf=medium to low, f=low, FF=very low.

The value of the volume $V_o$ of the crystallographic mesh of the zeolite prior to calcination depends on the substitution of the silicon by the tetravalent element.

TABLE

| X-ray diffraction pattern | | | |
|---|---|---|---|
| Extreme values of $d_{hkl}$ (nm) | $I/I_o$ | Extreme values of $d_{hkl}$ (nm) | $I/I_o$ |
| 1.112–1.133 | F | 0.356–0.362 | f |

TABLE-continued

X-ray diffraction pattern

| Extreme values of $d_{hkl}$ (nm) | $I/I_o$ | Extreme values of $d_{hkl}$ (nm) | $I/I_o$ |
|---|---|---|---|
| 0.988–1.014 | F | 0.343–0.349 | f |
| 0.969–0.983 | mF | 0.340–0.346 | m |
| 0.886–0.908 | f | 0.330–0.336 | m |
| 0.734–0.752 | m | 0.327–0.334 | m |
| 0.699–0.713 | f | 0.321–0.327 | mf |
| 0.660–0.677 | f | 0.314–0.319 | ff |
| 0.627–0.639 | m | 0.310–0.316 | ff |
| 0.597–0.611 | m | 0.300–0.306 | m |
| 0.591–0.603 | m | 0.294–0.299 | m |
| 0.564–0.576 | m | 0.291–0.296 | mf |
| 0.548–0.562 | m | 0.282–0.288 | ff |
| 0.530–0.541 | ff | 0.276–0.280 | ff |
| 0.510–0.520 | ff | 0.270–0.275 | ff |
| 0.492–0.503 | mf | 0.257–0.262 | f |
| 0.454–0.464 | mf | 0.253–0.258 | f |
| 0.438–0.488 | ff | 0.248–0.252 | f |
| 0.432–0.440 | mf | 0.247–0.251 | f |
| 0.420–0.429 | m | 0.238–0.241 | f |
| 0.394–0.404 | mf | 0.237–0.240 | f |
| 0.390–0.397 | f | 0.203–0.207 | ff |
| 0.397–0.387 | FF | 0.198–0.202 | mf |
| 0.372–0.379 | mF | 0.197–0.201 | m |
| 0.368–0.375 | mF | | |
| 0.361–0.368 | mF | | |

The precursors of zeolites can be produced by a method comprising:
(i) preparing a reaction mixture in an aqueous medium, containing at least one source of silicon having an oxidation state of +4, a source of the tetravalent element, fluoride ions and a structuring agent; and wherein the pH of the reaction mixture ranges from 1.5 to 12.0 and preferably from 6.0 to 11.0.
(ii) crystallizing the reaction mixture and recovering the crystalline precipitate therefrom.

The molar ratios of the various species in the reaction medium are those indicated above.

The crystalline precipitate is advantageously washed to remove impurities, particularly cations or anions which are unbonded or incorporated within the structure.

The product is easy to handle and is used, principally, to produce a zeolite by calcination under appropriate conditions, which are determined according to the required application of the zeolite.

The zeolites of the invention may be used for the catalysis of many reactions, such as dismutation or alkylation reactions, hydrogenolysis and hydrogenation of petroleum fractions or in reforming processes.

The present invention also features the use of the subject zeolites as catalysts for the hydroxylation of phenols or phenol others by reacting same with hydrogen peroxide.

Thus, another object of the invention is the provision of improved technique for hydroxylating phenols or phenol ethers in the presence of the above catalysts.

It more particularly relates to the hydroxyration of phenols or phenol ethers having the general formula (V):

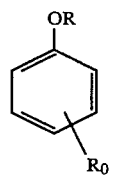

in which R is a hydrogen atom, a methyl radical, an ethyl radical or a phenyl radical and $R_0$ is a hydrogen atom, an alkyl radical ranging from 1 to 4 carbon atoms, an alkoxy radical having from 1 to 4 carbon atoms or a phenyl or cyclohexyl radical.

According to the invention, the phenol or phenol ether or formula (V) is reacted with hydrogen peroxide, in the presence of a catalytically effective amount of a zeolite of MFI structure, based on silica and an oxide of a tetravalent element and having the formula (I), and more preferably in the presence of a stannozeosilite of formula (Ia) or a zirconozeosilite of formula (Ib).

The hydrogen peroxide may be used in the form of an aqueous solution, in which the concentration of hydrogen peroxide is typically greater than 20% by weight. The hydrogen peroxide may be used equally as well in the form of a solution in an organic solvent. Exemplary organic solvents which may be used with the hydrogen peroxide are esters, particularly alkyl or cycloalkyl esters of saturated aliphatic carboxylic acids; it is preferred to use alkyl acetates and propionates having a total of 4 to 8 carbon atoms, or mixtures of such esters. It is also possible to use solutions of hydrogen peroxide in an ether, such as dioxane, diisopropylether or methyltertbutylether.

The molar ratio formula (V) compound/hydrogen peroxide advantageously ranges from 25/1 to 3/1 and preferably from 20/1 to 4/1.

The amount of stannozeosilite or zirconozeosilite according to the invention which may be employed in this process may vary very widely.

When the process is discontinuous, the weight of catalyst advantageously ranges from 0.1 to 20% of the weight of the formula (V) compound. This weight ratio preferably ranges from 0.5% to 10%. However, if the process is continuous, for example where a mixture of compound (V) and hydrogen peroxide solution is reacted on a fixed bed of catalyst, the catalyst/compound (V) ratios are immaterial, and there may at any given moment exist an excess by weight of catalyst relative to compound (V).

It is also possible to hydroxylate the compound (V) in a solvent therefor, which solvent is preferably miscible or partially miscible with water.

Exemplary such solvents include water; alcohols such as methanol, tertbutanol, isopropanol or ethanol; ketones such as acetone or methylisobutylketone; nitriles such as acetonitrile; carboxylic acids such as acetic acid; esters such as propyl acetate; ethers such as methyl-tertbutylether; polar aprotic solvents such as tetrahydrothiophene dioxide (sulfolane), ethylene glycol carbonate, propylene glycol carbonate or N-methylpyrrolidone.

The temperature at which the reaction is carried out typically ranges from 45° to 160° C. at atmospheric pressure. It is also possible to conduct the reaction at a higher temperature and at a pressure above atmospheric.

The phenols and phenol ethers which are preferably used in the process of the invention are those of formula (V) in which R is a hydrogen atom, a methyl radical or an ethyl radical, and $R_0$ is a hydrogen atom, a methyl ethyl or tertbutyl radical or a methoxy or ethoxy radical.

Exemplary thereof are phenol, anisole, orthocresol, metacresol, paracresol, 4-tertbutyl phenol, 2-methoxy phenol and 4-methoxy phenol.

The process of the invention is particularly well adopted for the preparation of hydroquinone and pyrocatechin.

In order to further illustrate the present invention and the advantages thereof, the following specific examples are given, it being understood that same are intended only as illustrative and in nowise limitative.

In said examples to follow, Examples 1 to 3 relate to stannozeosilites and process for the production thereof; Example 4 relates to a zirconozeosilite and a process for the production thereof; Example 5 relates to the use of the stannozeosilite of Example 1 as a catalyst for the hydroxylation of phenol; and Example 6 relates to the use of a zirconozeosilite as a catalyst for the hydroxylation of phenol.

EXAMPLE 1

This example describes the synthesis of a stannozeosilite in an acid medium, using $F^-$ ions as a mobilizing agent.

0.26 g of tin chloride $SnCl_4$ was added, drop by drop and with strong agitation, to a solution containing:
(i) 13.2 g of tetrapropylammonium bromide (TPA-Br);
(ii) 11 g of ammonium fluoride $NH_4F$;
(iii) 120 g of water;
(iv) 6 g of AEROSIL 130 silica marketed by DEGUSSA.

When the gel had been homogenized, 0.12 g of an MFI zeolite, namely, zeosilite, was added as seed crystals.

The pH of the reaction mixture was 8.5.

The molar ratios in the reaction mixture were as follows:

Sn/Si=0.01;

F/Si=3.0;

TPA+/Si=0.5;

$H_2O$/Si=70.

The reaction mixture was transferred into an autoclave, the internal surface of which being coated with polytetrafluoroethylene.

It was heated for 1 day at 200° C.

The pH of the medium when the autoclave was opened was 9.0.

After filtration, washing with water and drying at 80° C., 6.6 g of stannozeosilite precursor of the pure MFI type were obtained; its X-ray diffraction pattern was as indicated in the above Table.

The crystals obtained were rods measuring 5×1 micron.

Chemical analysis of the product indicated it had a fluorine content of 1.0%.

This precursor was calcined at 550° C. for 6 hours, thereby removing the structuring agent and restoring the porosity of the stannozeosilite obtained.

EXAMPLE 2

A composite gel was prepared, containing the element Si and Sn. Thus, 2.6 g of tin chloride $SnCl_4$ in 20 g of anhydrous methanol, then 15.2 g of silicon tetramethylate $Si(OCH_3)_4$ were added gradually with agitation. After homogenization, a solution containing 15 g of a 25% aqueous ammonia solution, 6 g of methanol and 10 g of water was added to the mixture. The gel solidified instantly. It was redispersed in water, then evaporated and dried at 120° C. The powder obtained was rewashed with water to remove any ammonium chloride formed. In this manner, about 10 g of a composite gel ($SiO_2$, $SnO_2$) was obtained, having a molar ratio Sn/Si=0.1.

The gel was dispersed in a solution containing 1.85 g of ammonium fluoride $NH_4F$, 3.32 g of water and 0.12 g of a zeolite, the zeolite being of MFI structure and serving as seed crystals.

The pH of the reaction mixtures was 7.

The molar ratios in the reaction mixture were:

Sn/Si=0.1;

F/Si=0.5;

TPA+/Si=0.125;

$H_2O$/Si=20.

The gel was heated for 6 days at 200° C.

The pH of the medium when the autoclave was opened was 9.5.

After filtration, washing with water and drying, 8.6 g of solid were obtained. Analysis by X-ray diffraction indicated that the solid was a precursor of MFI zeolite having the pattern indicated in the Table, and that a crystallized impurity of the $SnO_2$ cassiterite type was present (less than 10%).

The crystals obtained were rods measuring 8×2 microns.

Point analysis by electronic microprobe evidenced the Si/Sn ratios within the crystals to range from 20 to 60. Chemical analysis of the product evidenced a fluorine content of 0.91%.

After calcination at 550° C. for 6 hours, a stannozeosilite was obtained.

EXAMPLE 3

A composite gel was prepared containing the elements Si and Sn, by the procedure described in Example 2. The gel was dispersed in a solution containing 1.85 g of $NH_4F$, 6.65 g of TPABr and 72 g of water.

The pH was 7.5.

The molar ratios in the reaction mixture were:

Sn/Si=0.1;

F/Si=0.5;

TPA+/Si=0.25;

$H_2O$/Si=40.

The gel was heated for 6 days at 200° C. in an oven fitted with an agitating system.

The pH of the mixture when the autoclave was opened was 9.

After filtration, washing and drying, 8.9 g of solid were obtained. Analysis by X-ray diffraction demonstrated that the solid was a precursor of MFI zeolite having a pattern as indicated in the Table, and that a crystallized impurity of the $ZnO_2$ cassiterite type was present.

The crystals obtained had a length of 1 to 10 microns and a width of 0.5 to 2 microns.

After calcination at 550° C. for 6 hours, a stannozeosilite was obtained.

EXAMPLE 4

This example describes the synthesis of a zirconozeosilite in an acid medium, using $F^-$ ions as a mobilizing agent.

0.23 g of zirconium chloride $ZrCl_4$ was added, drop by drop and with strong agitation, to a solution containing:
 (i) 13.2 g of tetrapropylammonium bromide (TPA-Br),
 (ii) 11 g of a 40% by weight aqueous solution of hydrofluoric acid,
 (iii) 75 g of water,
 (iv) 6 g of AEROSIL 130 silica marketed by DEGUSSA.

After homogenization, 78 g of a 40% aqueous solution of methylamine were added, and 0.12 g of an MFI zeolite, namely, a zeosilite, as seed crystals.

The pH of the reaction mixture was 11.0.

The molar ratios in the reaction mixture were as follows:

$Zr/Si = 0.01$;

$F/Si = 3.0$;

$TPA^+/Si = 0.5$;

$H_2O/Si = 70$;

$CH_3NH_2/Si = 10$.

The reaction mixture was transferred into an autoclave internally coated with polytetrafluorethylene.

It was heated for 1 day at 200° C.

The pH of the medium when the autoclave was opened was 11.5.

After filtration, washing with water and drying at 80° C., 6.0 g of a precursor of MFI type zirconozeosilite was obtained, having the X-ray diffraction pattern indicated in the Table.

The crystals obtained were wafers measuring 5×2.5 microns.

Point analysis by electronic microprobe evidenced the Si/Zr ratio within the crystals to be about 140.

This precursor was calcined at 550° C. for 6 hours, thereby removing the structuring agent and restoring the porosity of the zirconozeosilite obtained.

EXAMPLE 5

Process of hydroxylating phenol:

A 30 cm³ pyrex glass reactor, provided with central agitation by a bar magnet, a cooler connected to a gas holder, a regulated heating system and an injection system, was first purged with nitrogen and then charged with:
 (i) 9.4 g of phenol (0.10 mol),
 (ii) 0.25 g of stannozeosilite prepared in Example 1.

The mixture was heated to 80° C. with agitation, then a 70% by weight per volume aqueous solution of $H_2O_2$ was injected therein (0.005 mol of $H_2O_2$).

It was then reacted for 2 hours, 30 minutes.

When the catalyst had been filtered, the unconverted $H_2O_2$ was determined by iodometry and the diphenols by high performance liquid chromatography (HPLC).

The following results were obtained:

| | | |
|---|---|---|
| (a) | Conversion rate (CR) of $H_2O_2$: | 61.0% |
| (b) | Yield of pyrocatechin relative to $H_2O_2$ converted (Y): | 23.0% |
| (c) | Yield of hydroquinone relative to $H_2O_2$ converted (Y): | 4.5% |
| (d) | Total yield of diphenols: | 27.5% |

EXAMPLE 6

Process of hydroxylating phenol:

The procedure of Example 5 was repeated exactly, except that the zirconozeolite of Example 4 was used instead of the stannozeosilite. Equivalent results were obtained, namely, an $H_2O_2$ degree of conversion of 62.0% and a total of diphenol yield of 28%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A calcined silica/oxide zeolite of MFI type having the formula (I):

$$(Si_{96-x}T'_x)O_{192} \qquad (I)$$

in which x is a number ranging from 0.1 to 5.0 and T' is tetravalent tin or tetravalent zirconium.

2. The silica/oxide zeolite as defined by claim 1, having the formula (Ia):

$$(Si_{96-x}Sn_x)O_{192} \qquad (Ia)$$

in which x is a number ranging from 0.1 to about 3.0.

3. The silica/oxide zeolite as defined by claim 1, wherein formula (Ia), x is a number ranging from 0.1 to 2.0.

4. The silica/oxide zeolite as defined by claim 1, having the formula (Ib):

$$(Si_{96-x}Zr_x)O_{192} \qquad (Ib)$$

in which x is a number ranging from 0.1 to about 4.0.

5. The silica/oxide zeolite as defined by claim 4, wherein formula (Ib), x is a number ranging from 0.1 to 2.0.

6. The silica/oxide zeolite as defined by claim 1, comprising a minor amount of fluorine values.

7. A silica/oxide zeolite of MFI type precursor having the formula (IV):

$$(Si_{96-x}T'_x)O_{192}, 4\pm1(S^+F^-) \qquad (IV)$$

in which x is a number ranging from 0.1 to 5.0, S+ is a structuring agent cation and T' is tetravalent tin or tetravalent zirconium.

8. The silica/oxide zeolite precursor as defined by claim 7, having the formula (IVa):

$$(Si_{96-x}Sn_x)O_{192}, 4\pm 1(S^+F^-) \tag{IVa}$$

in which x is a number ranging from 0.1 to about 3.0.

9. The silica/oxide zeolite precursor as defined by claim 8, wherein formula (IVa), x is a number ranging from 0.1 to 2.0.

10. The silica/oxide zeolite precursor as defined by claim 7, having the formula (IVb):

$$(Si_{96-x}Zr_x)O_{192}, 4\pm 1(S^+F^-) \tag{IVb}$$

in which x is a number ranging from 0.1 to about 4.0.

11. The silica/oxide zeolite precursor as defined by claim 10, wherein formula (IVb), x is a number ranging from 0.1 to 2.0.

12. The silica/oxide zeolite precursor as defined by claim 7, comprising from 0.01% to 1.3% by weight of fluorine values.

13. The silica/oxide zeolite precursor as defined by claim 7, having an orthohombic crystalline structure.

14. The silica/oxide zeolite precursor as defined by claim 13, having the X-ray diffraction pattern indicated in the Table.

15. The silica/oxide zeolite precursor as defined by claim 7, wherein formula (IV), S+ is a tertiary amine or quaternary ammonium cation, or cation of a phosphorus compound corresponding thereto.

16. A process for the preparation of the silica/oxide zeolite as defined by claim 1, comprising (i) providing an aqueous reaction medium containing a source of silicon in an oxidation state of 4+, a source T' of tetravalent tin or tetravalent zirconium, fluoride ions F, and a structuring agent S, in the molar ratios T'/(Si+T') ranging from 0.001 to 0.20, F/(Si+T') ranging from 0.02 to 6 and S/(Si+T') ranging from 0.002 to 4, said aqueous reaction medium having a pH ranging from about 1.5 to about 12.0, (ii) crystallizing a precipitate from such aqueous reaction medium, and (iii) calcining said crystalline precipitate at a temperature above 450° C.

17. The process as defined by claim 16, said molar ratio T'/(Si+T') ranging from 0.005 to 0.1.

18. The process as defined by claim 17, said molar ratio F/(Si+T') ranging from 0.06 to 2.

19. The process as defined by claim 18, said molar ratio S/(Si+T') ranging from 0.04 to 1.

20. The process as defined by claim 16, the molar ratio H₂O/(Si+T') in said aqueous reaction medium ranging from 4 to 400.

21. The process as defined by claim 20, said molar ratio ranging from 10 to 200.

22. The process as defined by claim 16, said aqueous reaction medium having a pH ranging from 6 to 11.0.

23. The process as defined by claim 16, said aqueous reaction medium comprising a pH-controlling amount of a base devoid of alkaline ions.

24. The process as defined by claim 23, said base comprising methylamine, dimethylamine, trimethylamine, ethylamine, diethylamine or triethylamine.

25. The process as defined by claim 23, the molar ratio base/(Si+T') in said aqueous reaction medium being less than 12.

26. The process as defined by claim 25, said molar ratio ranging from 0.1 to 8.

27. The process as defined by claim 16, said structuring agent S having the formula (II):

in which A is a nitrogen or phosphorus atom, and R₁, R₂, and R₃, which may be identical or different, are each a straight or branched chain alkyl radical having from 1 to 6 carbon atoms.

28. The process as defined by claim 16, said structuring agent S having the formula (III):

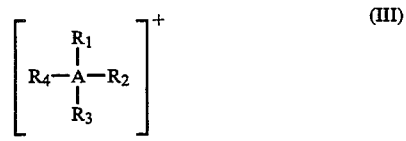

in which A is a nitrogen or phosphorus atom, and R₁, R₂, R₃ and R₄, which may be identical or different, are each a straight or branched chain alkyl radical having from 1 to 6 carbon atoms.

29. The process as defined by claim 27, wherein formula (III), A is a nitrogen atom.

30. The process as defined by claim 28, wherein formula (III), A is a nitrogen atom.

31. The process as defined by claim 16, said aqueous reaction medium comprising a common source of silicon and tetravalent tin or tetravalent zirconium.

32. The process as defined by claim 16, wherein said aqueous reaction medium, said source of silicon comprises a silica hydrogel, aerogel or xerogel, a colloidal suspension of silica, a silica ester, a water soluble silicate, a natural or synthetic silica, or a hydrolyzable tetravalent silicon compound.

33. The process as defined by claim 16, said aqueous reaction medium containing a source of tetravalent tin which comprises a crystalline or amorphous oxide or hydroxide of tin, a tin halide, a tin alcoholate or a soluble tin salt.

34. The process as defined by claim 16, said aqueous reaction medium containing a source of tetravalent zirconium which comprises a crystalline or amorphous oxide or hydroxide of zirconium, a zirconium alcoholate or a soluble zirconium salt.

35. The process as defined by claim 31, said aqueous reaction medium comprising a silica/tin glass or composite gel.

36. The process defined by claim 31, said aqueous reaction medium comprising a silica/zirconium glass or composite gel.

37. The process as defined by claim 16, said aqueous reaction medium comprising hydrofluoric acid, an amine or quaternary ammonium hydrofluoride or a compound hydrolyzable into fluoride anions.

38. The process as defined by claim 37, said aqueous reaction medium comprising a hydrolyzable tin fluoride or Silicon fluoride.

39. A process for the preparation of the silica/oxide zeolite precursor as defined by claim 7, comprising (i) providing an aqueous reaction medium containing a source of silicon in an oxidation state of 4+, a source of tetravalent tin or tetravalent zirconium, fluoride ions, and a structuring agent S, in the molar ratios T'/(Si+T') ranging from 0.001 to 0.20, F/(Si+T') ranging from 0.02 to 6 and S/(Si+T') ranging from 0.002 to 4, said aqueous reaction medium having a pH ranging from about 1.5 to about 12, (ii) crystallizing a precipitate from such aqueous reaction medium, and (iii) recovering said crystalline precipitate.

40. A process for the hydroxylation of a phenol or phenol ether, comprising reacting such phenol or phenol ether with hydrogen peroxide in the presence of a catalytically effective amount of the silica/oxide zeolite as defined by claim 1.

41. The process as defined by claim 40, said phenol or phenol ether having the formula (IV):

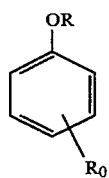

(V)

in which R is a hydrogen atom or a methyl, ethyl or phenyl radical, and $R_0$ is a hydrogen atom, an alkyl or alkoxy radical having from 1 to 4 carbon atoms, or a phenyl or cyclohexyl radical.

42. The process as defined by claim 41, wherein formula (V), R is a hydrogen atom or a methyl or ethyl radical and $R_0$ is a hydrogen atom, a methyl, ethyl or tertbutyl radical, or a methoxy or ethoxy radical.

43. The process as defined by claim 41, said phenol or phenol ether having the formula (V) comprising phenol, anisole, orthocresol, metacresol, paracresol, 4-tertbutylphenol, 2-methoxyphenol or 4-methoxyphenol.

44. The process as defined by claim 41, wherein the amount by weight of said silica/oxide zeolite ranges from 0.1% to 20% by weight of said phenol or phenol ether (V).

45. The process as defined by claim 44, said amount by weight of said silica/oxide zeolite ranging from 0.5% to 10% by weight of said phenol or phenol ether (V).

* * * * *